(12) United States Patent
Plumptre

(10) Patent No.: US 11,813,438 B2
(45) Date of Patent: Nov. 14, 2023

(54) DRUG DELIVERY DEVICE

(71) Applicant: Sanofi-Aventis Deutschland GMBH, Frankfurt am Main (DE)

(72) Inventor: David Aubrey Plumptre, Worcestershire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 615 days.

(21) Appl. No.: 16/414,687

(22) Filed: May 16, 2019

(65) Prior Publication Data

US 2019/0307966 A1 Oct. 10, 2019

Related U.S. Application Data

(63) Continuation of application No. 15/137,262, filed on Apr. 25, 2016, now Pat. No. 10,293,112, which is a
(Continued)

(30) Foreign Application Priority Data

Aug. 31, 2012 (EP) .................................. 12182568

(51) Int. Cl.
*A61M 5/315* (2006.01)
*A61M 5/24* (2006.01)
*A61M 5/31* (2006.01)

(52) U.S. Cl.
CPC .......... *A61M 5/31541* (2013.01); *A61M 5/24* (2013.01); *A61M 5/3155* (2013.01);
(Continued)

(58) Field of Classification Search
CPC .... A61M 5/31541; A61M 5/24; A61M 5/178; A61M 5/2429; A61M 5/31525;
(Continued)

(56) References Cited

U.S. PATENT DOCUMENTS

| 533,575 A | 2/1895 | Wilkens |
| 4,865,591 A | 9/1989 | Sams |

(Continued)

FOREIGN PATENT DOCUMENTS

| CA | 2138528 | 12/1998 |
| CA | 2359375 | 7/2000 |

(Continued)

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.
(Continued)

*Primary Examiner* — Tiffany Legette
(74) *Attorney, Agent, or Firm* — Fish & Richardson P.C.

(57) ABSTRACT

The invention relates to a disposable drug delivery device for selecting and dispensing a number of user variable doses of a medicament. The device comprises a housing, a cartridge holder for retaining a cartridge containing the medicament, a piston rod displaceable relative to the cartridge holder, a driver coupled to the piston rod, a display member for indicating a set dose and being coupled to the housing and to the driver, and a button coupled to the display member and to the driver.

10 Claims, 9 Drawing Sheets

Related U.S. Application Data continuation of application No. 14/423,733, filed as application No. PCT/EP2013/067863 on Aug. 29, 2013, now Pat. No. 9,345,838.

(60) Provisional application No. 61/697,087, filed on Sep. 5, 2012.

(52) U.S. Cl.
CPC .... *A61M 5/31525* (2013.01); *A61M 5/31551* (2013.01); *A61M 5/31568* (2013.01); *A61M 5/31585* (2013.01); *A61M 2005/3126* (2013.01)

(58) Field of Classification Search
CPC ............ A61M 5/3155; A61M 5/31551; A61M 5/31568; A61M 5/31585; A61M 2005/3126; A61M 2005/2485; A61M 2005/1787
See application file for complete search history.

(56) References Cited

U.S. PATENT DOCUMENTS

| | | | |
|---|---|---|---|
| 5,092,842 | A | 3/1992 | Bechtold et al. |
| 5,226,895 | A | 7/1993 | Harris |
| 5,226,896 | A | 7/1993 | Harris |
| 5,279,586 | A | 1/1994 | Balkwill |
| 5,304,152 | A | 4/1994 | Sams |
| 5,320,609 | A | 6/1994 | Haber et al. |
| 5,378,233 | A | 1/1995 | Haber et al. |
| 5,383,865 | A | 1/1995 | Michel |
| 5,391,157 | A | 2/1995 | Harris et al. |
| 5,480,387 | A | 1/1996 | Gabriel et al. |
| 5,505,704 | A | 4/1996 | Pawelka et al. |
| 5,582,598 | A | 12/1996 | Chanoch |
| 5,626,566 | A | 5/1997 | Petersen et al. |
| 5,637,087 | A * | 6/1997 | O'Neil .................. A61M 5/282 604/82 |
| 5,674,204 | A | 10/1997 | Chanoch |
| 5,688,251 | A | 11/1997 | Chanoch |
| 5,807,346 | A | 9/1998 | Frezza |
| 5,820,602 | A | 10/1998 | Kovelman et al. |
| 5,851,079 | A | 12/1998 | Horstman et al. |
| 5,921,966 | A | 7/1999 | Bendek et al. |
| 5,957,896 | A | 9/1999 | Bendek et al. |
| 5,961,495 | A | 10/1999 | Walters et al. |
| 6,004,297 | A | 12/1999 | Steenfeldt-Jensen et al. |
| 6,193,698 | B1 | 2/2001 | Kirchhofer et al. |
| 6,221,046 | B1 | 4/2001 | Burroughs et al. |
| 6,235,004 | B1 | 5/2001 | Steenfeldt-Jensen et al. |
| 6,248,095 | B1 | 6/2001 | Giambattista et al. |
| 6,562,006 | B1 | 5/2003 | Hjertman et al. |
| 6,613,023 | B2 | 9/2003 | Kirchhofer et al. |
| 6,699,224 | B2 | 3/2004 | Kirchhofer et al. |
| 6,899,698 | B2 | 5/2005 | Sams |
| 6,932,794 | B2 | 8/2005 | Giambattista et al. |
| 6,936,032 | B1 | 8/2005 | Bush, Jr. et al. |
| 7,169,132 | B2 | 1/2007 | Bendek et al. |
| 7,241,278 | B2 | 7/2007 | Moller |
| 7,678,084 | B2 | 3/2010 | Judson et al. |
| 7,850,662 | B2 | 12/2010 | Veasey et al. |
| 7,955,303 | B2 | 6/2011 | Burren et al. |
| 8,187,233 | B2 | 5/2012 | Harms et al. |
| 8,317,757 | B2 | 11/2012 | Plumptre |
| 9,005,171 | B2 | 4/2015 | Jones |
| 9,089,651 | B2 | 7/2015 | Butler et al. |
| 9,345,838 | B2 | 5/2016 | Plumptre |
| 10,293,112 | B2 | 5/2019 | Plumptre |
| 2002/0052578 | A1 | 5/2002 | Moller |
| 2002/0120235 | A1 | 8/2002 | Enggaard |
| 2003/0050609 | A1 | 3/2003 | Sams |
| 2004/0059299 | A1 | 3/2004 | Moller |
| 2004/0097883 | A1 | 5/2004 | Roe |
| 2004/0210199 | A1 | 10/2004 | Atterbury et al. |
| 2004/0267207 | A1 | 12/2004 | Veasey et al. |
| 2005/0107658 | A1 | 5/2005 | Brockway |
| 2005/0113765 | A1 | 5/2005 | Veasey et al. |
| 2006/0153693 | A1 | 7/2006 | Fietcher et al. |
| 2007/0016143 | A1 | 1/2007 | Miller et al. |
| 2007/0123829 | A1 | 5/2007 | Atterbury et al. |
| 2008/0021325 | A1 | 1/2008 | Drost |
| 2008/0077095 | A1 | 3/2008 | Kirchhofer |
| 2008/0133006 | A1 | 6/2008 | Crosby et al. |
| 2008/0210892 | A1 * | 9/2008 | Wagner .................. G21F 5/015 250/515.1 |
| 2009/0143745 | A1 * | 6/2009 | Langan .................. A61M 5/31 604/404 |
| 2009/0209939 | A1 * | 8/2009 | Verespej ............... A61M 5/326 604/506 |
| 2009/0247951 | A1 | 10/2009 | Kohlbrenner et al. |
| 2009/0254044 | A1 | 10/2009 | Kohlbrenner et al. |
| 2009/0264828 | A1 * | 10/2009 | Dette ................. A61M 5/31551 604/189 |
| 2009/0270804 | A1 * | 10/2009 | Mesa .................. A61M 5/3202 604/111 |
| 2009/0275916 | A1 | 11/2009 | Harms et al. |
| 2009/0275946 | A1 | 11/2009 | Duncan |
| 2010/0210947 | A1 | 8/2010 | Burcher et al. |
| 2010/0222634 | A1 | 9/2010 | Poirier |
| 2010/0324493 | A1 * | 12/2010 | Plumptre .......... A61M 5/31585 604/207 |
| 2010/0324495 | A1 * | 12/2010 | Jones ................. A61M 5/31551 604/207 |
| 2010/0331786 | A1 * | 12/2010 | Plumptre ............ A61M 5/3158 29/428 |
| 2011/0092905 | A1 | 4/2011 | Cowe |
| 2011/0178361 | A1 | 7/2011 | Yomtov |
| 2012/0143146 | A1 | 6/2012 | Strehl et al. |
| 2012/0165744 | A1 | 6/2012 | Jones |
| 2012/0165750 | A1 | 6/2012 | Plumptre |
| 2012/0172809 | A1 | 7/2012 | Plumptre |
| 2012/0289908 | A1 | 11/2012 | Kouyoumjian et al. |
| 2013/0197448 | A1 | 8/2013 | Butler et al. |
| 2013/0211327 | A1 | 8/2013 | Osman et al. |
| 2013/0267905 | A1 | 10/2013 | Teucher et al. |
| 2015/0057619 | A1 | 2/2015 | Osman et al. |
| 2015/0065960 | A1 | 3/2015 | Osman |

FOREIGN PATENT DOCUMENTS

| | | |
|---|---|---|
| CN | 1780652 | 5/2003 |
| CN | 102083489 | 6/2011 |
| CN | 102448516 | 5/2012 |
| CN | 102458532 | 5/2012 |
| CN | 102458534 | 5/2012 |
| EP | 0496141 | 7/1992 |
| EP | 538885 | 4/1993 |
| EP | 0897729 | 2/1999 |
| EP | 0937471 | 8/1999 |
| EP | 0937476 | 8/1999 |
| EP | 1046403 | 10/2000 |
| EP | 1776975 | 4/2007 |
| JP | S61-022844 | 1/1986 |
| JP | H05-137725 | 6/1993 |
| JP | 2005-068709 | 3/2005 |
| JP | 2006-116347 | 5/2006 |
| JP | 2008-529687 | 8/2008 |
| JP | 2009-507581 | 2/2009 |
| JP | 2009-515632 | 4/2009 |
| JP | 2009-297456 | 12/2009 |
| JP | 2010-503433 | 2/2010 |
| JP | 2011-519600 | 7/2011 |
| WO | WO 93/07922 | 4/1993 |
| WO | WO 93/24160 | 12/1993 |
| WO | WO 99/38554 | 8/1999 |
| WO | WO 01/10484 | 2/2001 |
| WO | WO 02/30495 | 4/2002 |
| WO | WO 02/092153 | 11/2002 |
| WO | WO 03/080160 | 10/2003 |
| WO | WO 2004/078241 | 9/2004 |
| WO | WO 2006/084876 | 8/2006 |

(56) References Cited

FOREIGN PATENT DOCUMENTS

| WO | WO 2007/057826 | 5/2007 |
| WO | WO 2009/132778 | 11/2009 |
| WO | WO 2010/139632 | 12/2010 |
| WO | WO 2010/139643 | 12/2010 |
| WO | WO 2010/149209 | 12/2010 |
| WO | WO 2010/149396 | 12/2010 |
| WO | WO 2012/049143 | 4/2012 |

OTHER PUBLICATIONS

Chinese Search Report for CN Application No. 2013800435948, dated Sep. 25, 2016.
International Preliminary Report on Patentability in International Application No. PCT/EP2013/067863, dated Mar. 3, 2015, 6 pages.
International Search Report for Int. App. No. PCT/EP2013/067863, completed Dec. 10, 2013.
Japanese Office Action for JP Application No. 2015-529018, dated Jul. 4, 2017.
International Preliminary Report on Patentability in International Appln. No. PCT/US2013/058253, dated Mar. 19, 2015, 6 pages.
International Search Report and Written Opinion in International Appln. No. PCT/US2013/058253, dated Dec. 19, 2013, 7 pages.

\* cited by examiner

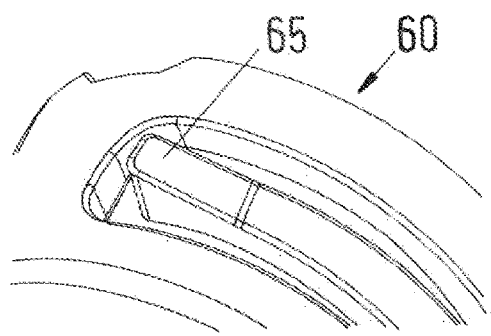
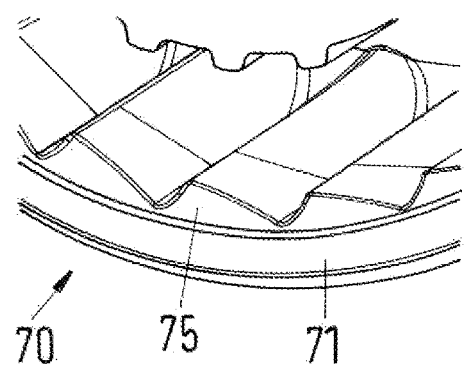
Fig.17a
Fig.17b
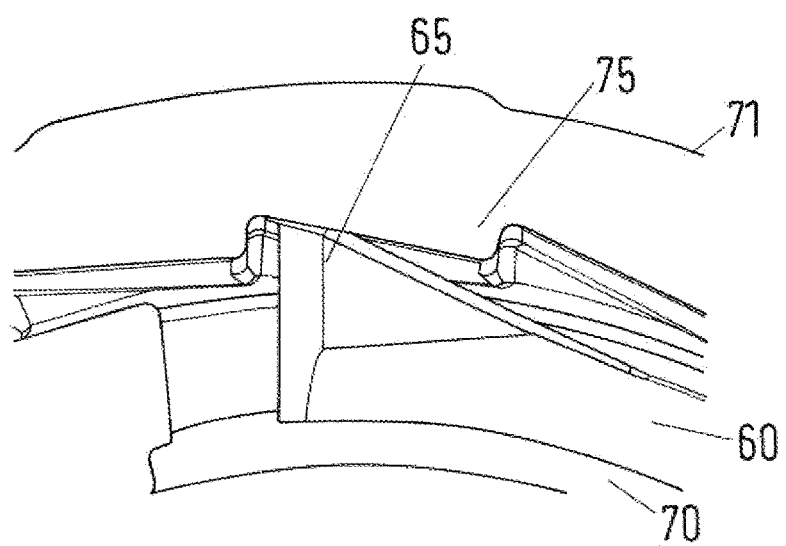
Fig.17c

DRUG DELIVERY DEVICE

CROSS REFERENCE TO RELATED APPLICATIONS

The present application is a continuation of U.S. patent application Ser. No. 15/137,262, filed Apr. 25, 2016, which is a continuation of U.S. patent application Ser. No. 14/423,733, filed Feb. 25, 2015, now U.S. Pat. No. 9,345,838, which is a U.S. National Phase Application pursuant to 35 U.S.C. § 371 of International Application No. PCT/EP2013/067863 filed Aug. 29, 2013, which claims priority to European Patent Application No. 12182568.1 filed Aug. 31, 2012, and U.S. Provisional Patent Application No. 61/697,078, filed Sep. 5, 2012. The entire disclosure contents of these applications are herewith incorporated by reference into the present application.

TECHNICAL FIELD

The present invention is generally directed to drug delivery devices. More particularly, the present invention is directed to disposable drug delivery devices.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present invention is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

Disposable and reusable drug delivery devices have certain perceived disadvantages. One perceived disadvantage is that such devices have a high number of parts and therefore such devices are typically complicated from a manufacturing and from an assembly standpoint. In addition, because such devices use a large number of components parts, such devices tend to be large and bulky, and therefore not easy to carry around or easy to conceal.

SUMMARY

A disposable drug delivery device according to the present invention typically comprises a housing, a cartridge holder for retaining a cartridge containing a medicament, a piston rod displaceable relative to the cartridge holder, a driver coupled to the piston rod, a display member for indicating a set dose and being coupled to the housing and to the driver, and a button coupled to the display member and to the driver. The device is delivered to the user in a fully assembled condition ready for use. Such a disposable drug delivery device is known e.g. from WO 2004/078241 A1.

It is an object of the present invention to provide an improved drug delivery device which has a reduced number of component parts and reduced manufacturing costs while also making the device less complex to assemble and manufacture. It is a further object to simplify the steps required for a user to set and dispense a dose while also making the device less complex and more compact in size.

According to a first embodiment of the present invention, this object is solved by a disposable drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, and a button coupled to the display member and to the driver, wherein the housing comprises an outer body and an inner body with the outer body being a one-piece component with the cartridge holder. Combining the cartridge holder and the outer body part of the housing into one single component reduces the number of component parts and thus assembling complexity. Further, the risk of a misuse, where a user attempts to exchange an empty cartridge in a disposable drug delivery device, is reduced.

According to a second embodiment of the present invention, this object is solved by a disposable drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, and a button coupled to the display member and to the driver, wherein the driver is in threaded engagement with the piston rod, permanently rotationally locked to the button and axially displaceable relative to the button in a proximal direction against the force of a resilient member which is a one piece component with either the driver or the button (or the button is displaceable relative to the driver in a distal direction). In other words, a spring or the like resilient member for biasing the button in a first direction which is usually provided as a separate component in known devices is integrated in the button or driver to thus reduce the number of component parts and assembling complexity.

Preferably, the driver comprises at least one elastically deformable finger having a free end engaging the button to bias the button in the proximal direction.

According to a third embodiment of the present invention, this object is solved by a disposable drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, and a button coupled to the display member and to the driver, wherein the housing comprises an inner surface with splines and the driver comprises at least one protrusion which in a first axial position of the button relative to the driver is allowed to elastically move in a radial direction and which in a second axial position of the button relative to the driver is forced by the button in a radially outer position thus rotationally locking the driver to the housing. In known devices a clutch member rotationally coupling the driver and the housing or a clicker member for producing a tactile and/or audible feedback during use of the device is usually provided with at least one separate component. In the present embodiment of the invention, these functions of the device are realized without adding component parts.

Preferably, the driver comprises at least one protrusion interacting with splines of the housing wherein the protrusion is elastically movable in a radial direction, and wherein the button comprises a recess or opening suitable for at least partly receiving the protrusion of the driver. If the button is moved relative to the driver, the protrusion cannot engage the recess or opening such that the radially inward movement of the protrusion is prevented, thus locking the protrusion in its radial position.

According to a fourth embodiment of the present invention, this object is solved by a disposable drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, and a button coupled to the display member and to the driver, wherein a first rotationally acting clutch is formed by the button and the display member which is in its coupled state during dose setting and in its decoupled state during dose dispensing, and a second rotationally acting clutch is formed by the driver and the housing which is in its decoupled state during dose setting and in its coupled state during dose dispensing. In known devices clutches usually require additional components either being interposed between the components to be coupled or decoupled or being used for actuation of the clutch. In contrast to that, with the present invention two clutches are provided without additional component parts.

Preferably, the button comprises a set of clutch teeth and the display member comprises a further set of corresponding clutch teeth, wherein axial movement of the button relative to the display member engages or disengages the sets of clutch teeth. The second clutch may be formed by the above mentioned at least one protrusion of the driver interacting with splines of the housing.

According to a fifth embodiment of the present invention, this object is solved by a disposable drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, and a button coupled to the display member and to the driver, wherein a first clicker, which is active during dose setting, is formed by the driver and the housing and a second clicker, which is active during dose dispensing, is formed by the button and the display member. In other words, a clicker for producing a tactile and/or audible feedback during use of the device is provided without adding separate components to the device.

According to a sixth embodiment of the present invention, this object is solved by a disposable drug delivery device for selecting and dispensing a number of user variable doses of a medicament, comprising a housing, a cartridge holder for retaining a cartridge containing the medicament, a piston rod displaceable relative to the cartridge holder, a driver coupled to the piston rod, a display member for indicating a set dose and being coupled to the housing and to the driver, and a button coupled to the display member and to the driver, wherein the number of components of the drug delivery device including the cartridge and a cap for shielding the cartridge holder is ten or less. In this respect, the cartridge including its movable rubber type bung, its pierceable rubber seal and e.g. its crimped annular metal band is considered as one component. Known disposable drug delivery devices usually comprise twelve or more parts, often nearly twenty separate component parts. Taking into account that disposable drug delivery devices are mass-produced, such a significant reduction of component parts results in reduced manufacturing costs.

The housing may comprise a transparent or translucent outer body, wherein at least a part of the outer body is coated by an opaque layer. This is especially preferred if the outer body is a one-piece component with usually the transparent or translucent cartridge holder. A further benefit of the outer body being transparent or translucent is that additional window inserts may be omitted. The opaque, i.e. not-transparent and not-translucent, layer may cover the part of the outer body containing the mechanical dosing components. Especially, the display member, which is typically provided with numbers or the like for displaying the set dose, may be at least partly shielded by the opaque layer such that only the number corresponding to the actually set dose is visible. The opaque layer may be an inner or outer coloured layer, a label or tag attached to the outer body, a lining attached or otherwise fixed to the outer body or a frosted or scarified surface.

Preferably, the piston rod is a double threaded piston rod having a first outer thread engaging an internal thread of the housing and a second outer thread engaging an internal thread of the driver, wherein the first and second outer threads may overlap each other at least partially. This allows to provide a mechanical advantage, i.e. a transmission (gear) ratio, in the device. Typically, the dial extension of the button, i.e. the distance the button winds out of the housing during dose setting, will be larger than the distance the piston rod is displaced relative to the cartridge holder and thus the cartridge. This allows dispensing even small amounts of a medicament with a maximum of dispensing control by the user.

A further reduction of the number of component parts may be achieved if the piston rod comprises a bearing attached to the piston rod by at least one predefined breakage point. The bearing is axially constrained but rotatable with respect to the piston rod after detachment of the bearing by destroying the at least one predefined breakage point during or after assembly. Thus, only one single component has to be handled during assembly which in use fulfils the function of two separate components.

According to a preferred embodiment, the driver is a tubular element having a distal portion engaging a nut interposed between the housing and the driver, and a proximal portion which at least partly surrounds a tubular portion of the button. Preferably, one of the housing and the driver comprises at least one spline and the other of the housing and the driver comprises a threaded portion with the nut interposed between the housing and the driver, wherein the nut comprises at least one protrusion engaging the at least one spline and a thread engaging the threaded portion, and wherein the threaded portion of the housing or the driver comprises a rotational end stop. If the nut abuts the rotational end stop, further movement of the nut in the thread is prevented which thus prevents further rotation of the driver relative to the housing which is required during dose setting. Thus, the nut may be used to limit the settable dose. This is e.g. required to prevent setting a dose exceeding the amount of medicament in the cartridge.

Preferably, one of the driver and the display member comprises a circular groove or a circular track defined by two walls and the other of the driver and the display member comprises a circular bulge engaging the groove or track. This allows to constrain the driver and the display member in the axial direction but to allow relative rotation.

If the housing comprises an outer body and an inner body, the inner body may be rotationally and axially constrained within the outer body such that a cylindrical gap exists between the inner body and the outer body. Preferably, the inner body comprises an outer thread engaging an inner thread of the display member and comprises at least one inner spline engaging a protrusion of the driver.

In a standard embodiment, the splines of the inner body are axially aligned with the pen device. In an alternative embodiment, it is possible to reduce dispense force, increase the velocity ratio and to increase the thread pitch of the display member (i.e. increase of friction coefficient asymptote), by providing the inner body with at least one inner spline which is helically twisted. In other words, the splines are not axially aligned, which results in the driver and the button traveling helically during dose dispensing. This may require adding an over-cap for the button as an additional component preventing relative rotation with respect to a user's hand, typically the thumb, during dose dispensing.

The basic function of the drug delivery device according to the present invention may include that a dose is selected by rotating a button component, which travels helically during dose setting. A dose may be delivered by pressing on the same button component, which now moves axially during dispensing. Preferably, any dose size can be selected, in predefined increments, between zero and a predefined maximum dose, e.g. 80 units. It is a further advantage if the mechanism permits cancelling of a dose without medicament being dispensed, e.g. by rotation of the button component in the opposite direction to when selecting a dose.

It is preferred if during dose setting the button is rotated which entrains the driver and the display member such that the button, the driver and the display member are moved on a helical path with respect to the housing and the piston rod. Further, during dose dispensing the button is axially displaced which entrains the driver and the display member such that the button, the driver and the display member are axially moved with respect to the housing and the piston rod, with the display member and the piston rod rotating with respect to the housing, the button and the driver.

To prevent malfunction or misuse of the device, the dose setting mechanism may be provided with stops preventing dialling of a dose below zero units or dialling of a dose above a maximum dose. Preferably, rotational hard stops are provided, e.g. between the display member and the inner body as a zero unit stop and/or as a maximum units stop.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Exemplary embodiments of the invention will now be described with reference to the accompanying drawings, in which:

FIGS. 17a-c show cut-away and sectional views of further details of the drug delivery device of FIG. 1.

DETAILED DESCRIPTION

Figure 2:
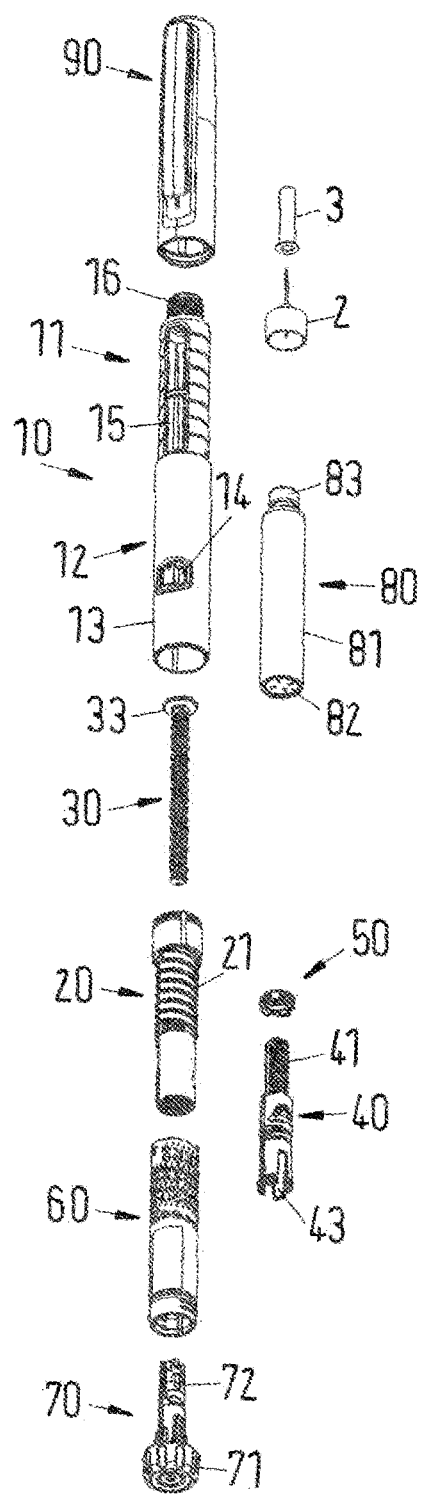
FIG. 2 shows in an exploded view the components of the drug delivery device of FIG. 1.
Figure 1:
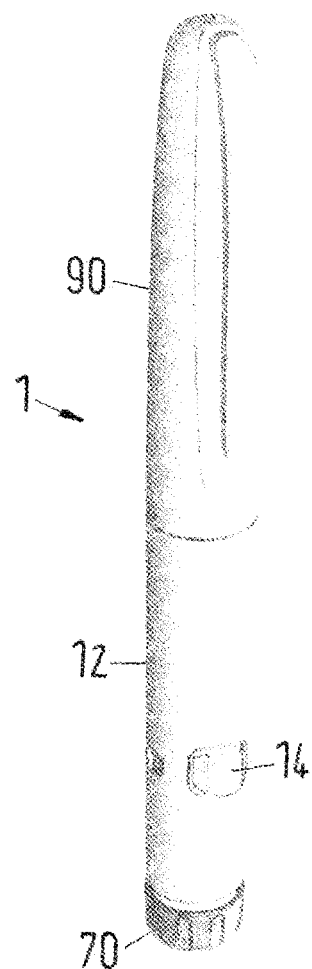
FIG. 1 shows a perspective view of a drug delivery device in accordance with the present invention.

FIG. 1 shows a drug delivery device 1 in the form of an injection pen. The device has a distal end (upper end in FIG. 1) and a proximal end (lower end in FIG. 1). The component parts of the drug delivery device 1 are shown in FIG. 2 in more detail. The drug delivery device 1 comprises an outer housing part 10, an inner body 20, a piston rod 30, a driver 40, a nut 50, a display member 60, a button 70, a cartridge 80 and a cap 90, i.e. in total nine separate component parts. As shown in FIG. 2, a needle arrangement comprising a needle hub 2 and a needle cover 3 may be provided as additional components, which can be exchanged as explained above.

The outer housing part 10 is a generally tubular element having a distal part, which forms a cartridge holder 11 for receiving cartridge 80, and a proximal part, which forms an outer body 12. In a preferred embodiment, the outer housing part 10 is transparent, with the outer body 12 being provided with an opaque layer 13. In FIG. 2, the opaque layer 13 covers most of the outer body 12 with the exception of a transparent window 14. Apertures 15 may be provided in the cartridge holder 11. Further, at its distal end the cartridge holder 11 has a thread 16 or the like for attaching the needle hub 2.

Figure 7:
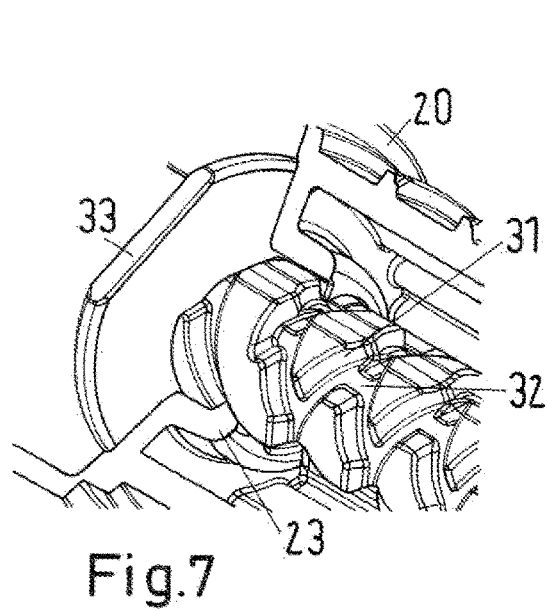
FIG. 7 shows a cut-away view of a detail of the drug delivery device of FIG. 1.
Figure 8:
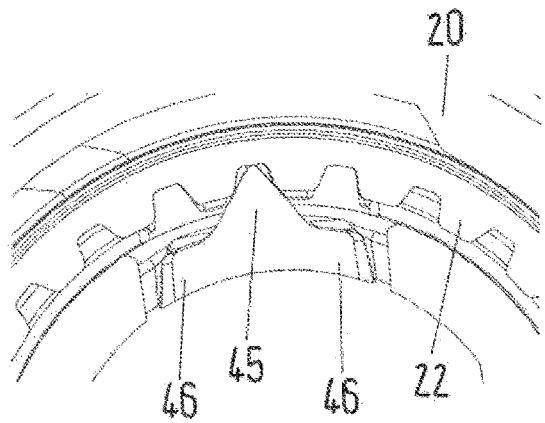
FIG. 8 shows a sectional view of a further detail of the drug delivery device of FIG. 1.
Figure 11:
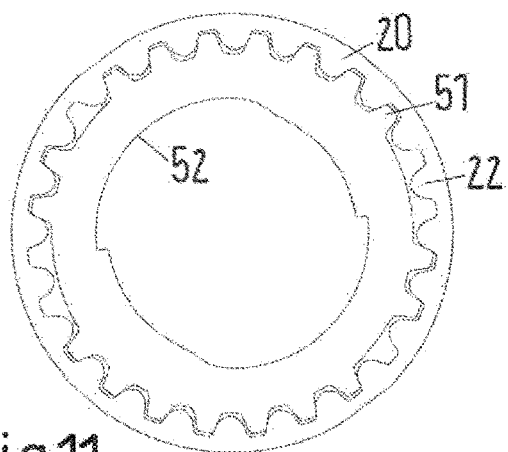
FIG. 11 shows a sectional view of the nut of FIG. 10.
Figure 16A:
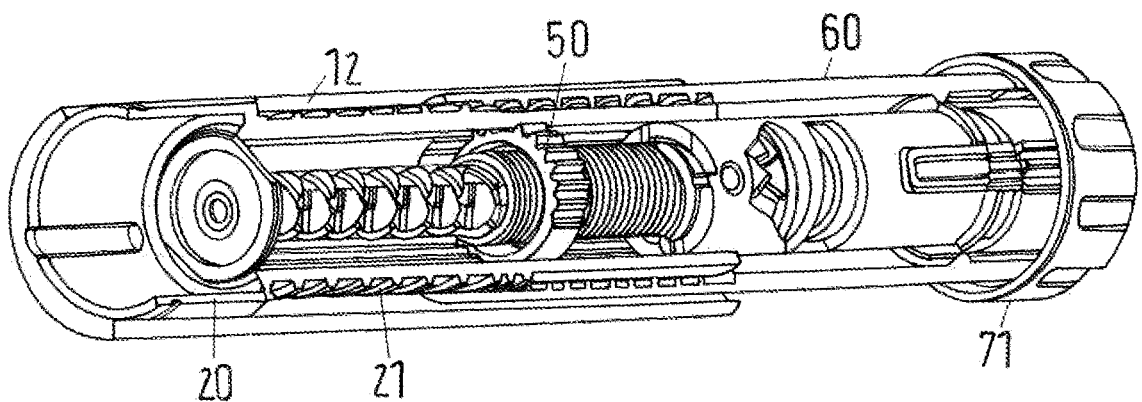
FIG. 16a shows a cut-away view of the proximal part of the drug delivery device of FIG. 1 in a maximum units position.
Figure 16B:
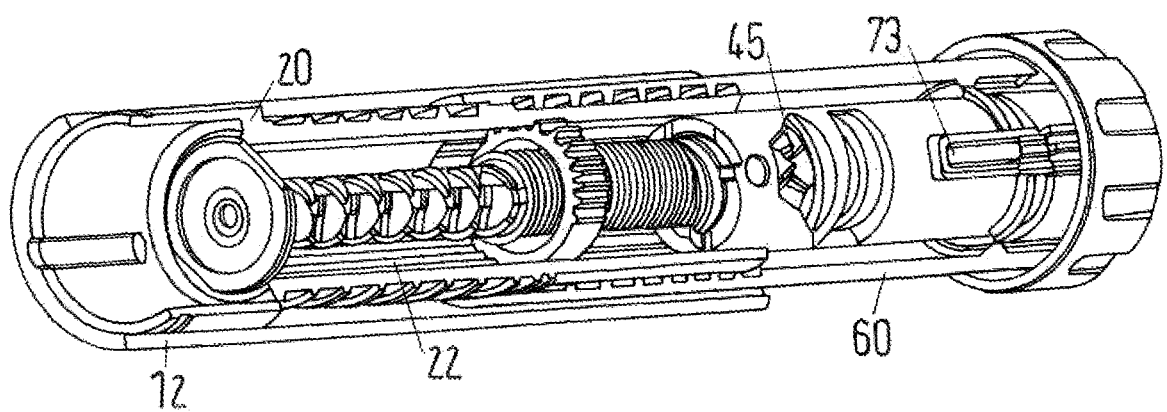
FIG. 16b shows a cut-away view of the proximal part of the drug delivery device of FIG. 1 in a maximum units position with the button pressed.
Figure 16C:
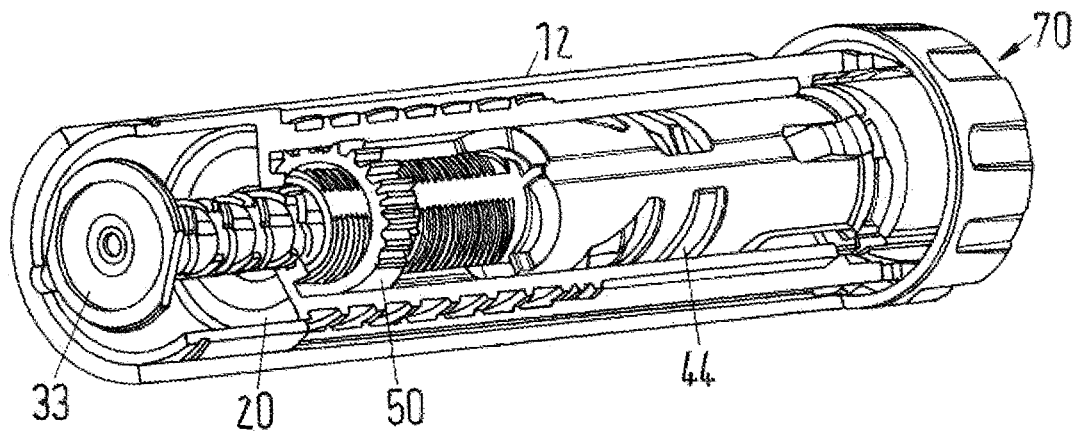
FIG. 16c shows a cut-away view of the proximal part of the drug delivery device of FIG. 1 in a zero unit position.

The inner body 20 is a generally tubular element having different diameter regions. As can be seen in FIGS. 16a to 16c, the inner body 20 is received in the outer body 12 and permanently fixed therein to prevent any relative movement of the inner body 20 with respect to the outer body 12. An external thread 21 is provided on the outer surface of the inner body 20. Further, splines 22 are provided on the inner surface of the inner body 20 which are shown in FIGS. 8 and 11. As can be taken from FIG. 7, the inner body 20 has near its distal end an inner thread 23.

The piston rod 30 is an elongate element having two external threads 31, 32 with opposite hand which overlap each other. One of these threads 31 engages the inner thread 23 of the inner body 20. A disk-like bearing 33 is provided at the distal end of the piston rod 30. As shown in FIG. 2, the bearing 33 may be attached to the piston rod 30 as a one-piece component via a predetermined breaking point. This allows that the bearing 33 is separated from the piston rod 30 such that the bearing 33 remains seated on the distal end of the piston rod 30 to allow relative rotation between the bearing 33 and the piston rod 30.

Figure 9A:
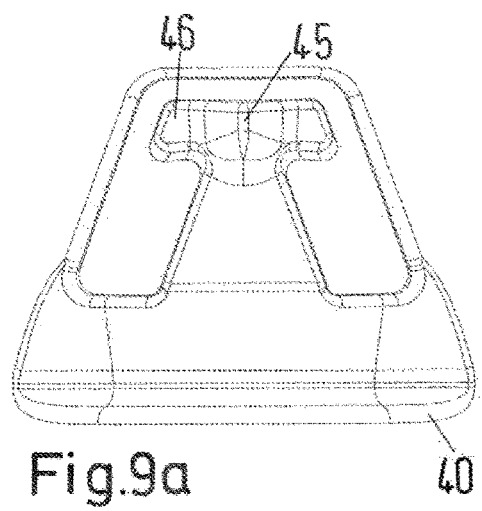
FIGS. 9a-d show cut-away views of further details of the drug delivery device of FIG. 1.
Figure 9B:
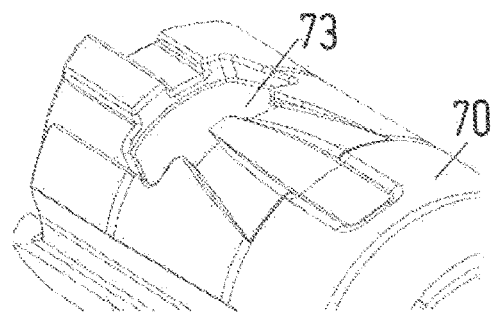
Figure 12A:
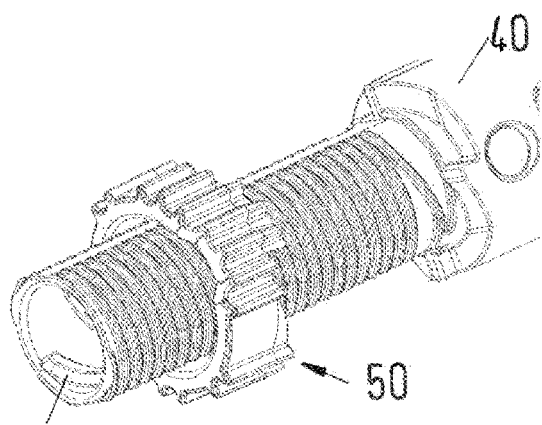
FIGS. 12a, b show cut-away views of further details of the drug delivery device of FIG. 1.
Figure 12B:
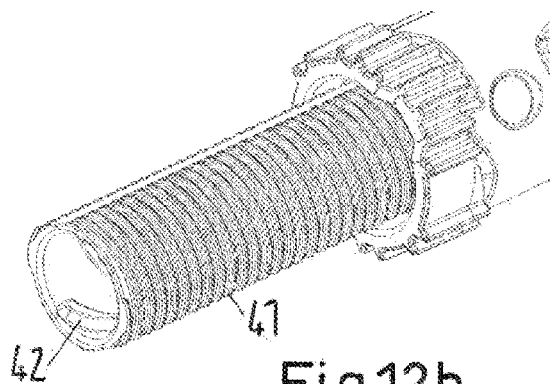

The driver 40 is a generally tubular element having different diameter regions. A distal region of the driver 40 has an external thread 41. An inner surface of the driver 40 has an inner thread 42 (FIGS. 12a and 12b) engaging one of the external threads 32 of the piston rod 30. The driver 40 surrounds the piston rod 30 and is at least partly located within inner body 20. The driver has at least one proximal opening 43 which will be explained in more detail below. Further, a resilient finger 44 (FIGS. 6a and 6b) is provided on the driver 40 by a U-shaped cut in the skirt of the driver 40. The finger 44 is allowed to flex in the axial direction and engages button 70. In addition, a flexibly hinged protrusion 45 (FIGS. 8 and 9a) is provided on the driver 40 by a similar cut out in the skirt of the driver 40. The protrusion 45 is allowed to flex radially inwardly and is provided with lateral flaps 46. Protrusion 45 engages splines 22 of the inner body 20.

Figure 10:
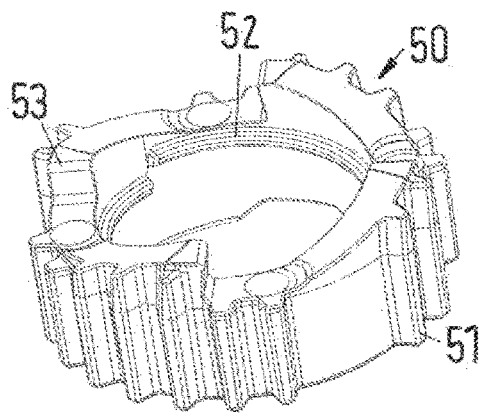
FIG. 10 shows a perspective view of a nut of the drug delivery device of FIG. 1.

The nut 50 is provided between the inner body 20 and the driver 40. External ribs 51 of the nut 50 engage splines 22 of the nut 50. An internal thread 52 of the nut engages the external thread 41 of the driver 40. As an alternative, splines and ribs could be provided on the interface between the nut 50 and the driver 40 and threads could be provided on the interface between the nut 50 and the inner body 20. As a further alternative, the nut 50 may be designed as e.g. a half nut. Further, in the embodiment of FIG. 10, four rotational hard stops 53 are provided on nut 50 for interaction with corresponding stops 47 on the driver 40 at the proximal end of thread 41.

The display member 60 is a generally tubular element with an internal thread 61 engaging the external thread 21 of the inner body 20. Thus, the display member 60 is interposed between the inner body 20 and the outer body 12. A series of numbers is provided, e.g. printed, on the outer surface of the display member 60. The numbers are arranged on a helical line such that only one number or only a few numbers are visible in through window 14 of the outer body 12. As will be explained in more detail below, the display member 60 is attached to the driver 40 preventing relative axial movement but allowing relative rotation.

Figure 4A:
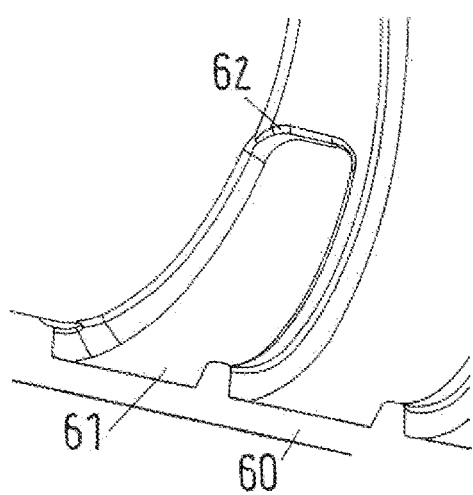
FIGS. 4a, b show sectional views of a detail of the drug delivery device of FIG. 1.
Figure 4B:
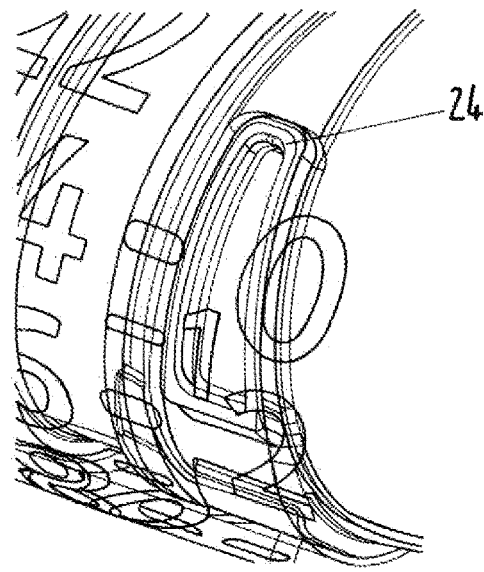
Figure 5A:
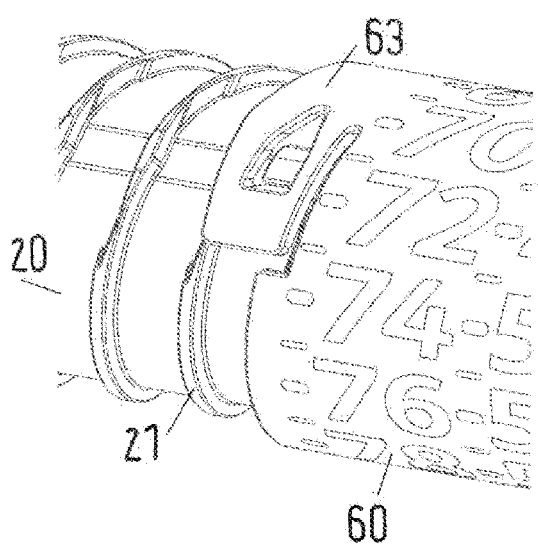
FIGS. 5a, b show sectional views of a further detail of the drug delivery device of FIG. 1.
Figure 5B:
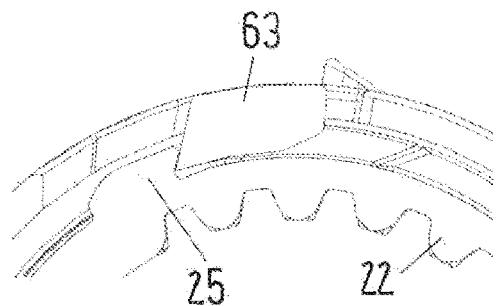

FIGS. 4a and 4b show in more detail a zero unit rotational hard stop formed by a stop wall 62 in thread 61 of the display member 60 and a corresponding stop face 24 on the inner body 20. FIGS. 5a and 5b show in more detail a maximum dose (e.g. a 80 units) rotational hard stop formed by a finger 63 at the distal end of the display member 60 and a protrusion 25 in thread 21 of the inner body 20. Thus, a user is prevented from dialing below zero units and above e.g. 80 units.

The button 70 has a proximal end with an, e.g. serrated, flange or outer skirt 71 allowing a user to easily grip and dial button 70. A sleeve-like part 72 of the button 70 with a reduced diameter extends in the distal direction and is inserted into the driver 40 such that a limited relative axial movement is allowed but relative rotation is prevented. This is achieved by a rib 73 on the sleeve-like part 72 which is guided in a proximal opening 43 of the driver 40. A recess 73 which generally has the outline of the protrusion 45 and its lateral flaps 46 is provided in the sleeve-like part 72 of button 70.

Figure 13A:
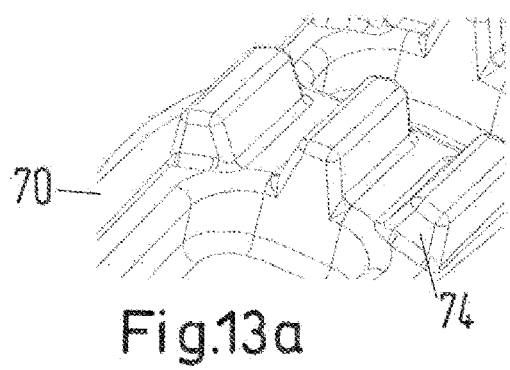
FIGS. 13a-c show cut-away views of further details of the drug delivery device of FIG. 1.
Figure 13B:
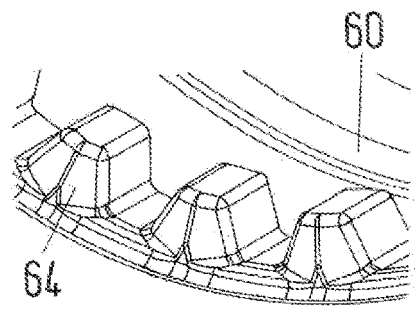

A clutch is provided between the display member 60 and the button 70 by corresponding teeth 64 and 74 (FIGS. 13a and 13b). If teeth 74 of the button 70 engage teeth 64 of the display member 60, these components are rotationally locked. The resilient finger 44 of the driver 40 biases the button 70 in the proximal direction of the device 1, i.e. in a direction engaging the clutch teeth. The clutch can be released allowing relative rotation by shifting the button 70 axially with respect to the display member 60 against the bias of finger 44.

Further, a dispense clicker is provided by flexible arms 65 on the display member 60 and a toothed profile 75 on the inner side of flange 71 of button 70. This clicker is shown in FIGS. 17a to 17c.

The cartridge 80 includes a pre-filled, necked-down cartridge reservoir 81, which may be typically made of glass. A rubber type bung 82 or stopper is located at the proximal end of the cartridge reservoir 81, and a pierceable rubber seal (not shown) is located at the other, distal, end. A crimped annular metal band 83 is used to hold the rubber seal in place. The cartridge 80 is provided within the cartridge holder 11 with bearing 33 of piston rod 30 abutting bund 82.

FIG. 1 shows the cap 90 attached to the distal end of the device 1, thus covering the cartridge holder 11. The cap 90 may be releasably snapped onto the outer housing 10 and can be taken off for use of the device 1.

In the following, the function of the disposable drug delivery device 1 and its components will be explained in more detail.

Figure 3A:
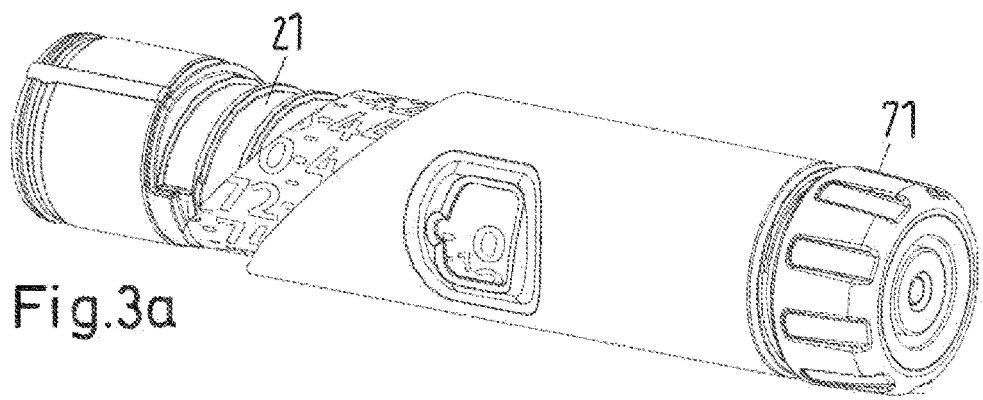
FIG. 3a shows a cut-away view of the proximal part of the drug delivery device of FIG. 1 in a zero unit position.
Figure 3B:
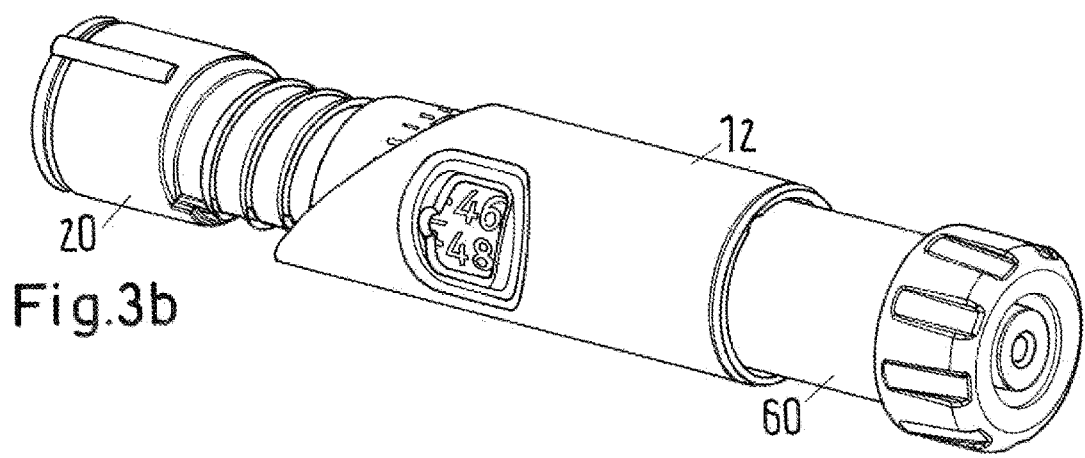
FIG. 3b shows a cut-away view of the proximal part of the drug delivery device of FIG. 1 in a 47 units position.
Figure 6A:
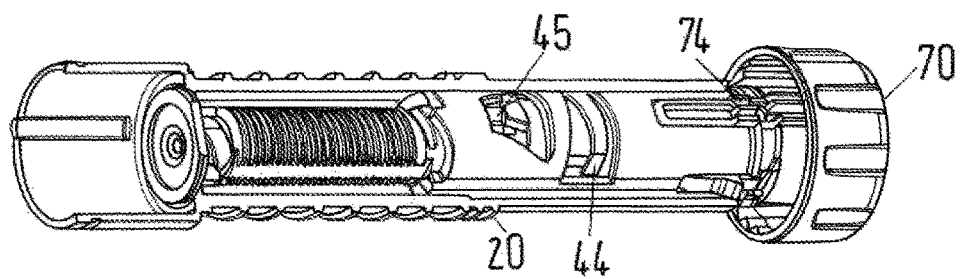
FIG. 6a shows a cut-away view of the proximal part of the drug delivery device of FIG. 1 in a zero unit position.

To use the device, a user has to select a dose. In the start (at rest) condition as shown in FIGS. 3a and 6a the display member 60 indicates the number of doses dialed to the user. The number of dialed units can be viewed through the dose window 14 in the outer body 12. Due to the threaded engagement between the display member 60 and the inner body 20 rotation of the button 70 in a clockwise fashion causes the display member 60 to wind out of the device and incrementally count the number of units to be delivered. FIG. 3b shows an intermediate stage of dialing (47 of 80 units).

During dose setting button 70, driver 40 and display member 60 are rotationally locked together via clutch teeth 64, 74. Further, button 70, driver 40 and display member 60 are axially coupled. Thus, these three components wind out of the outer housing 10 during dose setting.

Clockwise rotation of the button 70 causes the driver 40 to rotate and in doing so it advances along the piston rod 30 which remains fixed throughout dialing.

The protrusion 45 and splines 22 form a clicker arrangement that provides tactile and audible feedback to the user when dialing doses. This clicker arrangement has the further functions of defining discrete positions for the display member 60 when dialing and of providing a method of locking the rotation of the driver 40 and hence button 70 when dosing. During dialing (dose setting) the button 70 is in an axial position relative to the driver 40 such that the pocket or recess 73 is located radially inwards of the protrusion. Thus, the protrusion 45 is allowed to flex radially inwards to overcome splines 22 thereby providing a tactile and audible feedback to the user. FIG. 8 shows the flexible protrusion arm 45 located between splines 22 which are e.g. 15° apart.

Figure 3C:
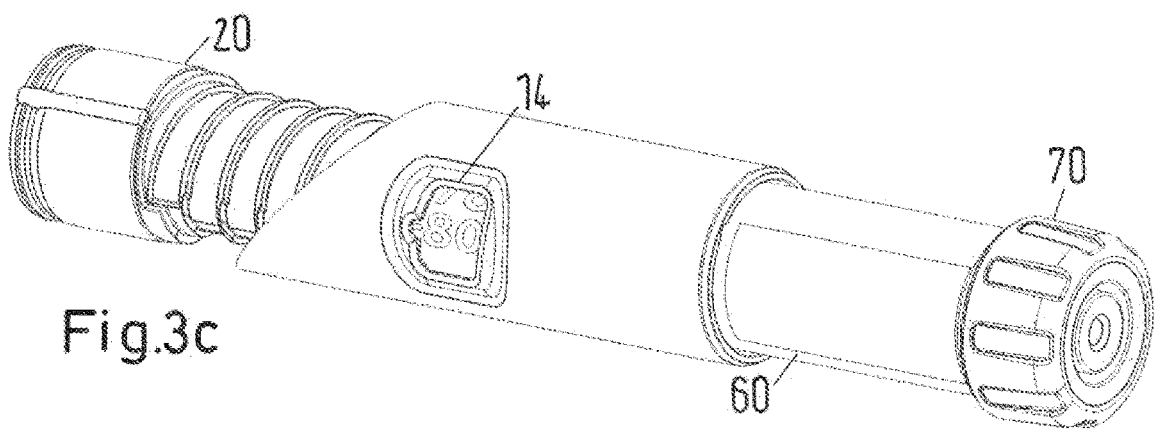
FIG. 3c shows a cut-away view of the proximal part of the drug delivery device of FIG. 1 in a maximum units position.
Figure 6B:
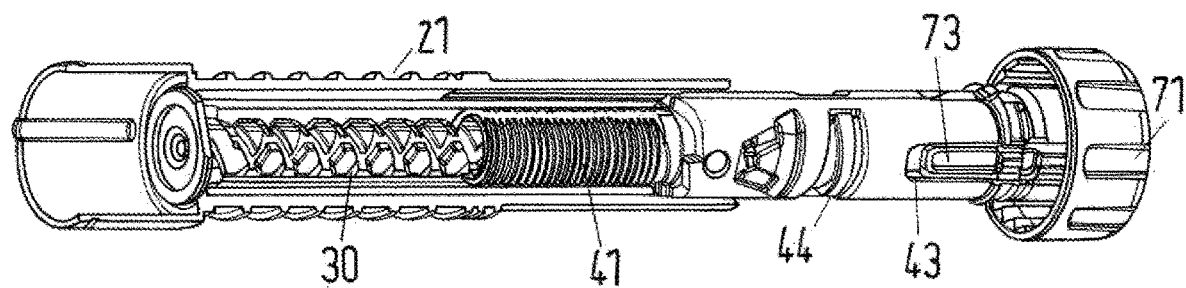
FIG. 6b shows a cut-away view of the proximal part of the drug delivery device of FIG. 1 in a maximum units position.

At the maximum settable dose of 80 units, the stop features 63, 25 shown in FIGS. 5a and 5b engage to prevent further dialing. This position of the device is shown in FIGS. 3c and 6b.

The last dose nut 50 provides the function of counting the number of dispensed units. The nut 50 locks the device 1 at the end of life and as such no more drug can be dialed or dispensed by the user. The last dose nut 50 and the driver 40 are connected via a threaded interface 41, 52 as explained above. Further, the last dose nut 50 is assembled into splines 22 as shown in FIG. 11 such that the nut 50 and the inner body 20 are rotationally locked together (at all times). Rotation of the driver 40 during dialing causes the nut 50 to advance along the driver 40 thread 41. The nut 50 is free to slide axially within the inner body 20 at all times which allows advancement of the nut. The change in pitch shown in FIGS. 12a and 12b towards the final doses axially accelerates the advancement of the nut 50 towards the end of life lockout condition. At the end of life condition, the stop features 53 of the last dose nut 50 contact the corresponding features 47 on the driver 40. The splined contact with inner body 20 reacts any torque transmitted by these stop features 47.

Figure 15A:
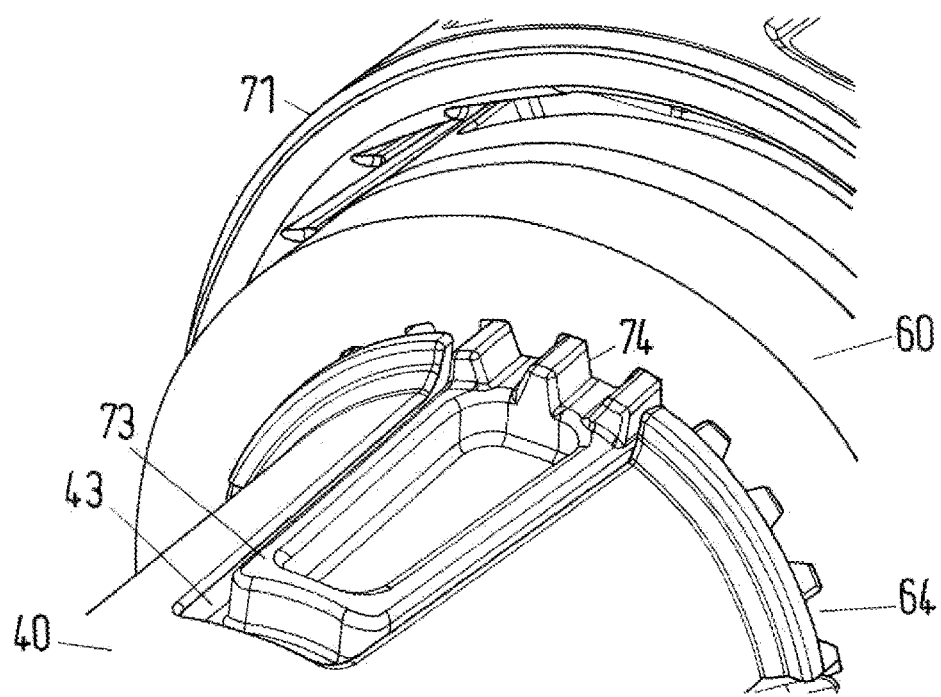
FIGS. 15a, b show cut-away views of further details of the drug delivery device of FIG. 1.
Figure 15B:
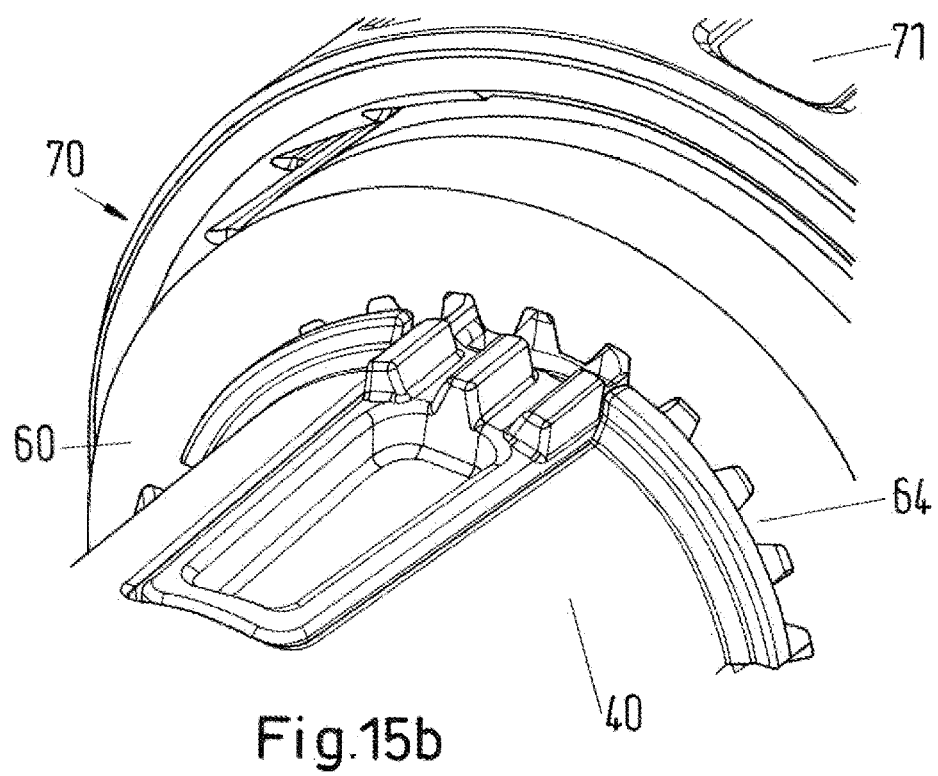

With the desired dose dialed, the device 1 is ready for dose dispensing. This basically requires pushing button 70 which will result in a disengagement of the clutch teeth 64, 74. As mentioned above, when dialing a dose the button 70 is 'biased out' and the clutch features 64, 74 which rotationally lock the driver 40, button 70 and display member 60 together are engaged as shown in FIG. 15a. Upon pressing the button 70 the clutch features 64, 74 disengage as shown in FIG. 15b and relative rotation between the display member 60 and the button 70 is possible. In all conditions the driver 40 and the button 70 are rotationally locked together by engagement rib 73 and opening 43. Thus, with the clutch 64, 74 disengaged (button 70 pushed in) button 70 and driver 40 are rotationally locked together with the button 70, the driver 40 and the display member 60 still being axially coupled.

Figure 9C:
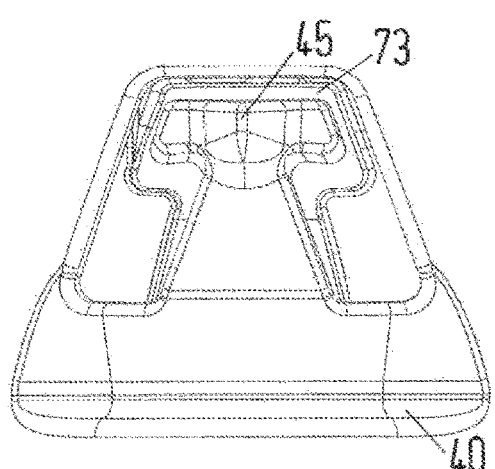
Figure 9D:
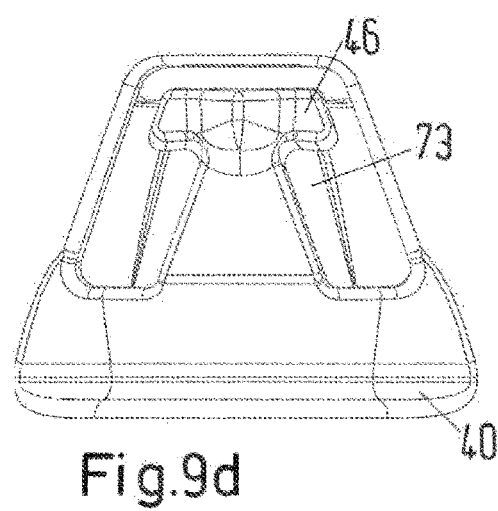
Figure 13C:
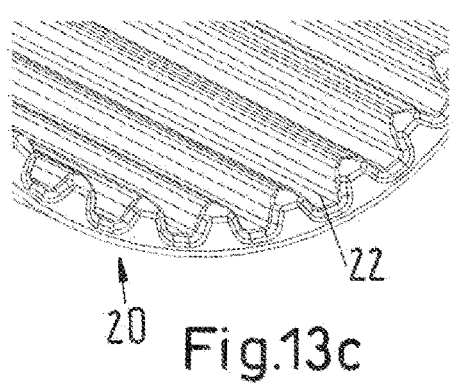
Figure 14:
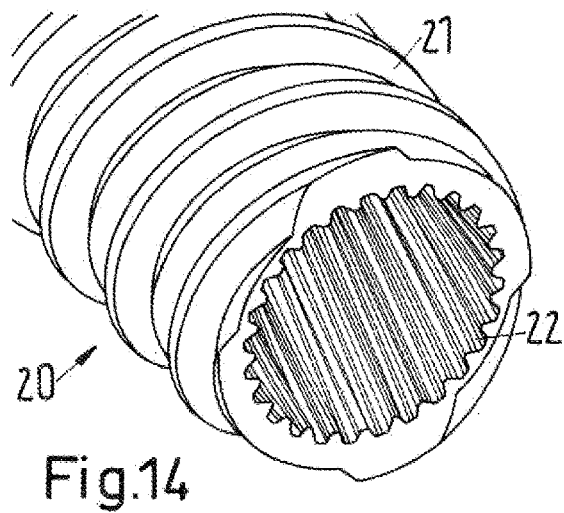
FIG. 14 shows a perspective view of a nut of the drug delivery device of FIG. 1.

At the same time the relative axial movement of the button 70 with respect to the driver 40 results in the pocket or recess 73 being shifted relative to the protrusion 45. Thus, the protrusion 45 is prevented from flexing inwards because flaps 46 rest on a non-recessed area of button 70. A comparison of FIGS. 9c and 9d shows this activation of the lockout feature preventing the flexible protrusion arm 45 from overcoming splines 22 if the button 70 is pressed. In this condition, the driver 40 and the button 70 are rotationally constrained to the inner body 20 thus preventing any rotation relative to the outer housing 10 if the splines 22 are axially aligned with the device as shown in FIG. 13c. The above mentioned alternative embodiment with twisted splines 22 is shown in FIG. 14.

With the desired dose dialed the button 70 can be depressed and the piston rod 30 driven forward to dispense drug from the cartridge. The interaction of mating threads between the piston rod 30, driver 40 and inner body 20 delivers a mechanical advantage of 2:1. The sequence of dispensing is depicted in FIGS. 16a to 16c with FIG. 16a showing the device 1 with 80 units dialed prior to pushing button 70, FIG. 16b shows the device 1 with 80 units dialed and button 70 pushed and FIG. 16c shows the device 1 with 80 units dispensed.

During dose dispensing a dispense clicker is active which involves button 70 and display member 60. The dispense clicker provides primarily audible feedback to the user that drug is being dispensed. The interaction between the flexible arms 65 on the display member 60 and the toothed profile 75 on the button flange 71 provide this dispense click. Relative rotation is only allowed in one direction. This occurs when the components are decoupled during dispense and a click is produced for every unit.

The invention claimed is:

1. A drug delivery device comprising:
   a housing;
   a dose setting mechanism operable by a user to select a dose of a medicament to be dispensed from the drug delivery device;
   a cartridge holder for retaining a pre-filled cartridge containing the medicament;
   a piston rod displaceable relative to the cartridge holder;
   a driver coupled to the piston rod;
   a display member for indicating the selected dose and being coupled to the housing and to the driver;
   a clutch mechanism that is formed by the display member and a button, wherein the button is coupled to the display member and the driver;
   wherein the housing comprises a transparent or translucent outer body which forms a one-piece component with the cartridge holder, and at least a part of the outer body is coated by an opaque layer;
   wherein the drug delivery device is a disposable device, and the pre-filled cartridge is not replaceable and not removable from the drug delivery device without destroying the drug delivery device, wherein a total quantity of components of the drug delivery device including the cartridge and a cap for shielding the cartridge holder is ten or fewer.

2. The drug delivery device of claim 1, wherein the opaque layer is an inner or outer coloured layer.

3. The drug delivery device of claim 1, wherein the opaque layer is a label or tag attached to the outer body.

4. The drug delivery device of claim 1, wherein the opaque layer is a lining attached or otherwise fixed to the outer body.

5. The drug delivery device of claim 1, wherein the opaque layer is a frosted or scarified surface.

6. The drug delivery device of claim 1, wherein the opaque layer covers a portion of the outer body containing mechanical dosing components.

7. The drug delivery device of claim 1, wherein the drug delivery device does not have a resettable dose setting mechanism.

8. The drug delivery device of claim 1, wherein the piston rod comprises a bearing attached to the piston rod by at least one breakage point.

9. The drug delivery device of claim 1, wherein the dose setting mechanism comprises the button.

10. The drug delivery device of claim 1, further comprising a spring integrated into the button or the driver and configured to bias the button in a first direction.

\* \* \* \* \*

UNITED STATES PATENT AND TRADEMARK OFFICE
CERTIFICATE OF CORRECTION

PATENT NO. : 11,813,438 B2  
APPLICATION NO. : 16/414687  
DATED : November 14, 2023  
INVENTOR(S) : David Aubrey Plumptre Page 1 of 1

It is certified that error appears in the above-identified patent and that said Letters Patent is hereby corrected as shown below:

On the Title Page

On page 2, Item (60), delete "61/697,087" and insert -- 61/697,078 --

Signed and Sealed this  
Twenty-first Day of October, 2025

John A. Squires  
*Director of the United States Patent and Trademark Office*